United States Patent
Raghuram et al.

(10) Patent No.: US 9,848,823 B2
(45) Date of Patent: Dec. 26, 2017

(54) CONTEXT-AWARE HEART RATE ESTIMATION

(71) Applicant: Apple Inc., Cupertino, CA (US)

(72) Inventors: Karthik Jayaraman Raghuram, Santa Clara, CA (US); James M. Silva, San Jose, CA (US); Alexander Kanaris, San Jose, CA (US); Barker N. Bhaskaran, Kerala (IN)

(73) Assignee: APPLE INC., Cupertino, CA (US)

( * ) Notice: Subject to any disclaimer, the term of this patent is extended or adjusted under 35 U.S.C. 154(b) by 123 days.

(21) Appl. No.: 14/812,870

(22) Filed: Jul. 29, 2015

(65) Prior Publication Data

US 2016/0058367 A1 Mar. 3, 2016

Related U.S. Application Data

(60) Provisional application No. 62/044,884, filed on Sep. 2, 2014.

(51) Int. Cl.
*A61B 5/02* (2006.01)
*A61B 5/00* (2006.01)
(Continued)

(52) U.S. Cl.
CPC ............ *A61B 5/486* (2013.01); *A61B 5/0205* (2013.01); *A61B 5/1118* (2013.01); *A61B 5/681* (2013.01); *A61B 5/721* (2013.01); *A61B 5/7246* (2013.01); *A61B 5/7278* (2013.01); *A61B 5/02438* (2013.01)

(58) Field of Classification Search
CPC . A61B 5/0205; A61B 5/02438; A61B 5/1118; A61B 5/486; A61B 5/681; A61B 5/721; A61B 5/7246; A61B 5/7278
See application file for complete search history.

(56) References Cited

U.S. PATENT DOCUMENTS

| 2014/0121543 A1* | 5/2014 | Chan | A61B 5/0006 600/483 |
| 2014/0275854 A1* | 9/2014 | Venkatraman | A61B 5/721 600/301 |

(Continued)

OTHER PUBLICATIONS

Comtois, Gary W., "Implementation of Accelerometer—Based Adaptive Noise Cancellation in a Wireless Wearable Pulse Oxirneter Platform for Remote Physiological Monitoring and Triage." A Thesis submitted to the faculty of Worcester Polytechnic Institute. Aug. 31. 2007. 149 pages.

(Continued)

*Primary Examiner* — George Manuel
(74) *Attorney, Agent, or Firm* — Kilpatrick Townsend & Stockton, LLP

(57) ABSTRACT

A device can estimate the heart rate of an active user by using a physiological model to refine a "direct" measurement of the user's heart rate obtained using a pulse sensor. The physiological model can be based on heart rate response to activity and can be informed by context information, such as the user's current activity and/or intensity level as well as user-specific parameters such as age, gender, general fitness level, previous heart rate measurements, etc. The physiological model can be used to predict a heart rate, and the prediction can be used to assess or improve the direct measurement.

19 Claims, 9 Drawing Sheets

(51) Int. Cl.
 *A61B 5/0205* (2006.01)
 *A61B 5/11* (2006.01)
 *A61B 5/024* (2006.01)

(56) References Cited

U.S. PATENT DOCUMENTS

2014/0296658 A1* 10/2014 Yuen ................. A61B 5/6885
 600/301
2015/0350822 A1  12/2015 Xiao et al.

OTHER PUBLICATIONS

Tapia, Emmanuel Munguia, "Using Machine Learning for Real-time Activity Recognition and Estimation of Energy Expenditure." Submitted to the Program in Media Arts and Sciences, School of Architecture and Planning, at the Massachusetts institute of Technology. Jun. 2008. 493 pages.

Lopez-Silva, Sonnia Maria, et. al., "Heuristic Algorithm for Photoplethysmographic Heart Rate Tracking During Maximal Exercise Test." Journal of Medical and Biological Engineering, 32(3): Accepted: Oct. 2, 2011. pp. 181-188.

Brage, Soren et al., "Branched Equation Modeling of Simultaneous Accelerometry and Heart Rate Monitoring Improves Estimate of Directly Measured Physical Activity Energy Expenditure." J. Appl. Physiol 96—Inoovative Methodology. First published Sep. 12, 2003. pp. 341-351.

Lee. Han-Wook, et al., "The Periodic Moving. Average Filter for Removing. Motion Artifacts from PPG Signals." International Journal of Control, Automation, and Systems, vol. 5, No. 6, Dec. 2007. pp. 701-706.

* cited by examiner

CONTEXT-AWARE HEART RATE ESTIMATION

CROSS-REFERENCES TO RELATED APPLICATIONS

This application claims the benefit of U.S. Provisional Application No. 62/044,884, filed Sep. 2, 2014, entitled "Context-Aware Heart Rate Estimation."

The present disclosure is related to U.S. Provisional Application No. 62/004,707, filed May 29, 2014, entitled "Electronic Devices with Motion Characterization Circuitry"; to U.S. Provisional Application No. 62/040,967, filed Aug. 22, 2014, entitled "Harmonic Template Classifier"; to U.S. application Ser. No. 14/466,890, filed Aug. 22, 2014, entitled "Heart Rate Path Optimizer"; and to U.S. Provisional Application No. 62/044,846, filed Sep. 2, 2014, entitled "Calibration and calorimetry Using Motion and Heart Rate Sensors." The disclosures of these applications are incorporated by reference in their entirety.

BACKGROUND

The present disclosure relates generally to heart rate estimation and in particular to context-aware heart rate estimation.

Many individuals in the modern world want to become more physically fit. Such individuals may engage in a variety of fitness activities. One popular form of fitness activity involves aerobic exercise, such as running, cycling, swimming, or the like. During aerobic exercise, the individual's heart rate can be used as a key metric for determining whether the individual is exercising at appropriate intensity. For example, many experts recommend exercising with enough intensity to maintain the heart rate in a range from about 65-85% of an age-dependent maximum heart rate. Knowing one's heart rate in real time can therefore be helpful in maximizing the benefits of aerobic exercise.

Knowing one's heart rate can have other benefits as well. For instance, resting heart rate (the heart rate when the person is sitting or lying still) can be a general indicator of overall cardiovascular health. Heart rate can also be used, in combination with other data, as an indicator of energy expenditure, allowing the individual to better understand his or her personal metabolism.

One traditional way to determine an individual's heart rate during exercise involves counting pulses felt at a pulse point such as the wrist or neck. For example, the individual can place one or more fingers over a pulse point and count pulses while watching a clock for a prescribed number of seconds; the heart rate can be determined, e.g., by dividing the pulse count by the elapsed time, by counting for ten seconds and multiplying by six to compute beats per minute, or the like. This, however, generally requires the user to pause, or at least slow down, the activity long enough to find a pulse and a clock or timer, making it inconvenient and disruptive to the continuity of the activity.

To alleviate this inconvenience, various devices exist that can monitor a user's heart rate. One type of heart rate sensor includes electrodes placed near or over the heart. The electrodes can be, for example, incorporated into a chest strap that the user wears, and the chest strap can communicate with a device worn in a more convenient location, such as on the user's wrist. Chest straps, however, are generally uncomfortable to wear, and this may limit the range of situations in which a user is likely to use the device. Another type of heart rate sensor is a fingertip "pulse oximetry" sensor. These sensors are often used in clinical settings to measure both pulse (heart rate) and hemoglobin oxygenation saturation using photoplethysmography ("PPG"). However, these types of sensors are generally not reliable when the wearer is moving around, so they are not considered ideal for use during physical activity.

SUMMARY

Certain embodiments of the present invention relate to systems and methods that facilitate reliable determination of the heart rate of an active user. In some embodiments, a "direct" measurement of the user's heart rate based on a pulse sensor (such as a PPG sensor) can be refined using a physiological model that is informed by context information, such as the user's current activity and/or intensity level as well as user-specific parameters such as age, gender, fitness level, previous heart rate measurements, and so on.

In some embodiments, a device can generate heart rate data samples using a pulse sensor (such as a PPG sensor). The device can determine a direct heart rate estimate based on the heart rate data samples. For instance, the device can perform noise reduction and frequency-spectrum analysis (e.g., a template matching analysis) to identify a most likely heart rate, and the direct heart rate estimate can be based on the most likely heart rate. The device can also determine an activity context for the user, such as the type of activity in which the user is engaged (e.g., walking, running, jogging, swimming, cycling, sitting, sleeping, etc.) and, where appropriate, an intensity associated with the activity. Based on the activity context and user-specific parameters (e.g., age, fitness level, previously measured heart rates), the device can determine a modeled heart rate estimate. This determination can be independent of the data gathered by the pulse sensor. The device can then determine a final heart rate estimate based on the direct heart rate estimate and the modeled heart rate estimate.

The following detailed description together with the accompanying drawings will provide a better understanding of the nature and advantages of the present invention.

DETAILED DESCRIPTION

Certain embodiments of the present invention relate to systems and methods that facilitate reliable determination of the heart rate of an active user. In some embodiments, a "direct" measurement of the user's heart rate based on a pulse sensor (such as a PPG sensor) can be refined using a physiological model that is informed by context information, such as the user's current activity and/or intensity level as well as user-specific parameters such as age, gender, fitness level, previous heart rate measurements, and so on.

In some embodiments, a device can generate heart rate data samples using a pulse sensor (such as a PPG sensor). The device can determine a direct heart rate estimate based on the heart rate data samples. For instance, the device can perform noise reduction and frequency-spectrum analysis (e.g., a template matching analysis) to identify a most likely heart rate, and the direct heart rate estimate can be based on the most likely heart rate. The device can also determine an activity context for the user, such as the type of activity in which the user is engaged (e.g., walking, running, jogging, swimming, cycling, sitting, sleeping, etc.) and, where appropriate, an intensity associated with the activity. Based on the activity context and user-specific parameters (e.g., age, fitness level, previously measured heart rates), the device can determine a modeled heart rate estimate. This determination can be independent of the data gathered by the pulse sensor. The device can then determine a final heart rate estimate based on the direct heart rate estimate and the modeled heart rate estimate.

Figure 1:
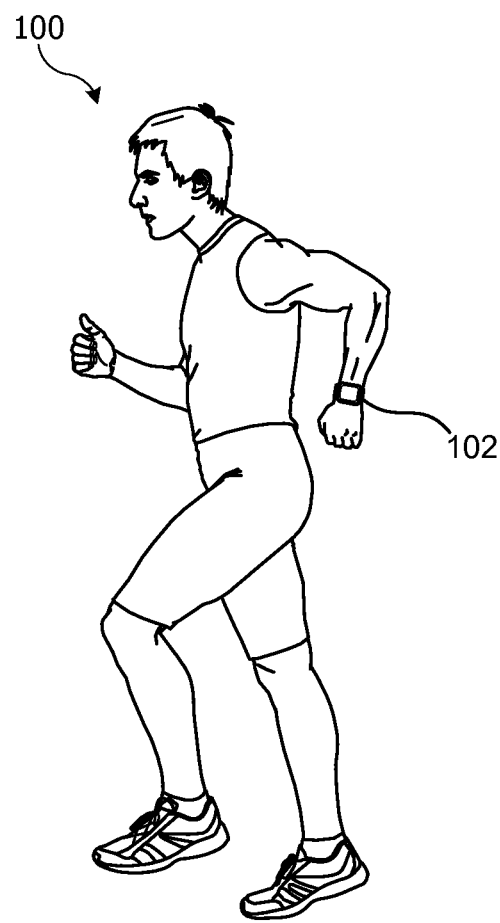
FIG. 1 shows a user wearing a wearable device that can provide heart rate monitoring according to an embodiment of the present invention

FIG. 1 shows a user 100 wearing a wearable device 102 that can provide heart rate monitoring according to an embodiment of the present invention. Wearable device 102 in this example is wearable on the user's wrist, although any device that can operate while the user is engaged in physical activity can be used in connection with embodiments of the invention. In this example, user 100 is running Like many runners, user 100 is interested in monitoring his performance. As described below, wearable device 102 can provide heart rate monitoring and other workout-related data.

Figure 2A:
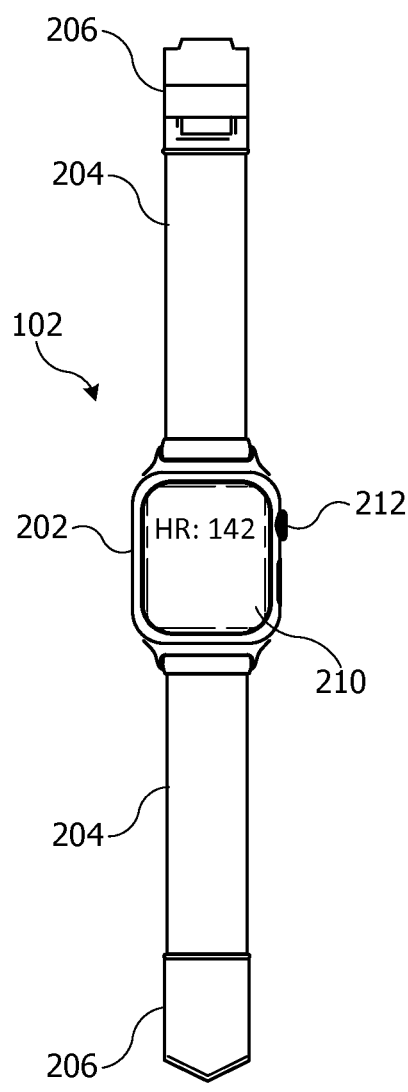
FIGS. 2A and 2B show a front view and back view, respectively, of a wearable device according to an embodiment of the present invention.
Figure 2B:
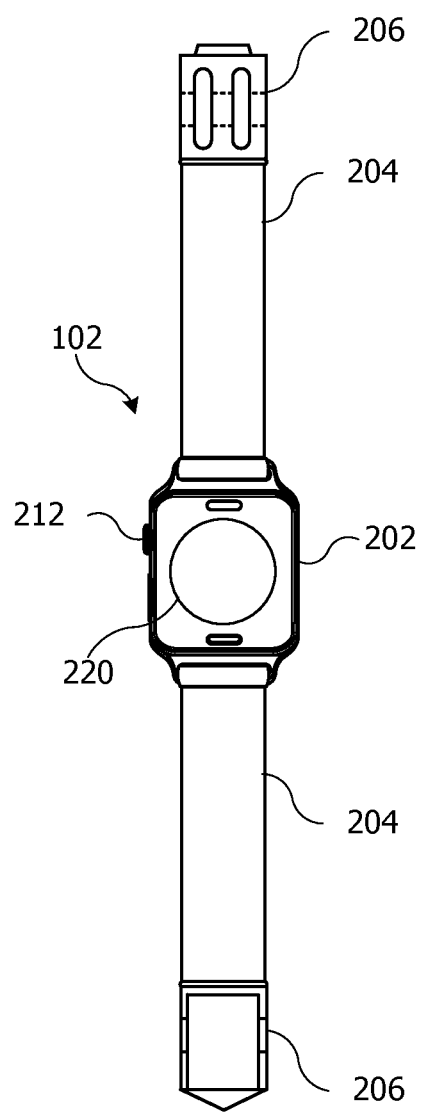

FIGS. 2A and 2B show a front view and back view of wearable device 102 according to an embodiment of the present invention. Wearable device 102 can have a body portion 202 and a strap 204. Strap 204 can be used to secure wearable device 102 to the user's wrist (e.g., as shown in FIG. 1) via clasp members 206 located at each end. In some embodiments, all electronic components of wearable device 102 (sensors, processing circuitry, communication circuitry, etc.) can be disposed within body portion 202. In other embodiments, strap 204 can also incorporate sensors and/or other electronic components for wearable device 102.

As shown in FIG. 2A, a front face of body portion 202 can provide a display 210 operable to present visual information to a user. In this example, display 210 can present the user's heart rate, which can be determined using techniques described herein. Other types of information can also be presented, such as duration of an activity (e.g., a workout), distance traveled or steps taken during the activity, calories burned, and/or other parameters related to the activity. Still other types of information can be unrelated to a workout or activity. For instance, in some embodiments wearable device 102 can pair with a companion device such as the user's mobile phone, and wearable device 102 can present notifications and other information received from the phone.

In some embodiments, display 210 can incorporate a touch screen, allowing display 210 to be operated as a user input device. For example, display 210 can provide various graphical control regions, that when touched by the user, invoke functions of wearable device 102. One or more mechanical input controls 212 can also be provided; examples include buttons, switches, rotary knobs, or the like.

As shown in FIG. 2B, a back face of body portion 202 can provide various sensors 220, which can be arranged as desired. Examples of sensors 220 include pressure sensors, skin conductance sensors, temperature sensors, and/or other biometric sensors. In some embodiments, sensors 220 can include a pulse sensor to detect the pulse or heart rate of a user wearing device 102; an example is described below. Other types of sensors can also be provided, in body portion 202 and/or strap 204.

Wearable device 102 can also incorporate other components not shown in FIG. 2, such as a speaker to produce audio output, a microphone to receive audio input, a camera or image sensor, an ambient light sensor, a communication interface (e.g., a wireless communication interface incorporating an antenna and supporting circuitry), a charging interface to charge an onboard battery of wearable device 102, a microprocessor, and so on.

It will be appreciated that wearable device 102 is illustrative and that variations and modifications are possible. The form factor and geometry can be modified as desired, as can the particular arrangement and combination of input and/or output components and sensors.

Figure 3:
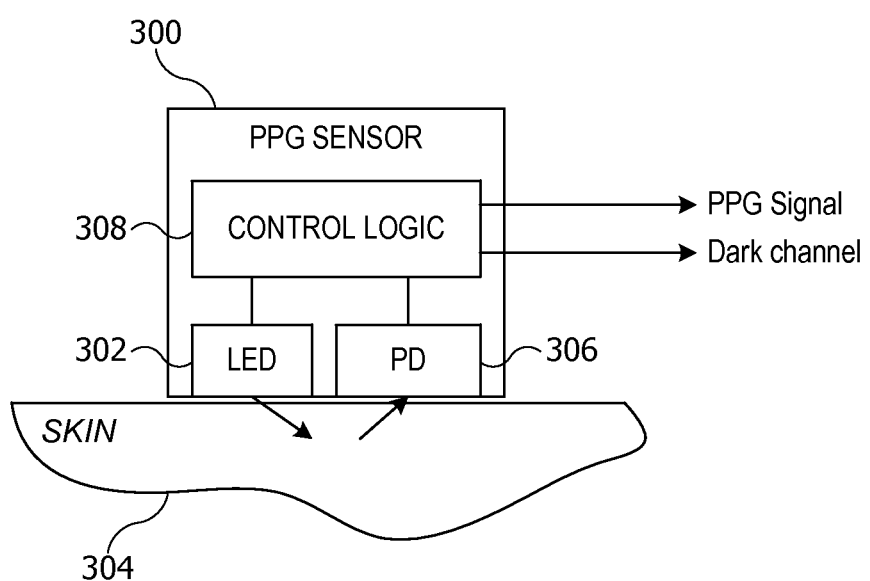
FIG. 3 is a simplified block diagram of a pulse sensor that can be incorporated into a wearable device according to an embodiment of the present invention.

As noted above, wearable device 102 can include a pulse sensor. FIG. 3 is a simplified block diagram of a pulse sensor 300 that can be incorporated into wearable device 102 according to an embodiment of the present invention. Pulse sensor 300 can be a photoplethysmographic (PPG) sensor that can detect a user's pulse or heart rate based on cyclic changes in skin reflectance and absorbance that occur due to variations in the pressure and volumetric occupancy of circulating blood in the user's arteries, microvasculature, and surrounding tissue. As a consequence of the cardiac cycle, these variations cause periodic distension and relaxation of the arteries and microvasculature, resulting in measurable cyclic variations in skin reflectance and absorbance.

PPG sensor 300 can include a light source (e.g., a conventional LED) 302 oriented to direct light onto a region of user's skin 304 and an optical sensor 306 (e.g., a conventional photodiode (PD)) oriented to detect light reflected from skin 304. Control logic 308 can be connected to LED 302 and PD 306. In operation, control logic 308 can provide a control signal to selectively turn on or off LED 302. Control logic 308 can receive light-level signals from PD 306 while LED 302 is either on or off. Control logic 308 can provide a PPG signal based on the light levels sensed by PD 306 while LED 302 is on and a "dark channel" signal based on the light levels sensed by PD 306 while LED 302 is off. As described below, the dark channel signal can be used for noise filtering. In some embodiments, control logic 308 can sample the light level sensed by PD 306 at regular intervals and provide the samples as outputs, e.g., in digital form. Dark channel and PPG signal samples can be provided separately, either via physically separate data paths or multiplexed onto a single path in a manner that allows the two sample types to be distinguished.

The basic operating principles of PPG are well known, and PPG is frequently used in clinical settings to measure the heart rate of a patient who is seated or lying down. It is also well known that once the patient starts moving, the reliability of PPG rapidly deteriorates. For instance, if a user is running or walking, relative motion between PPG sensor 300 and skin 304 can create cyclical changes in signal strength that can mimic a pulse. Additionally, periodic deformations in local tissue structures through which the probing optical signals are transmitted can introduce signals resembling those caused by the cardiac cycle. Such effects can result in a less reliable measurement of the user's heart rate.

Accordingly, certain embodiments of the present invention provide systems and methods that improve the reliability of PPG signals in the presence of user activity. In some embodiments, a "direct" measurement of the user's heart rate based on a PPG sensor can be refined using a heart rate estimate determined from a physiological model that is informed by activity context information, such as the user's current activity and/or intensity level. The model can also incorporate user-specific parameters such as age, gender, general fitness level, historic heart rate measurements, and so on.

Figure 4:
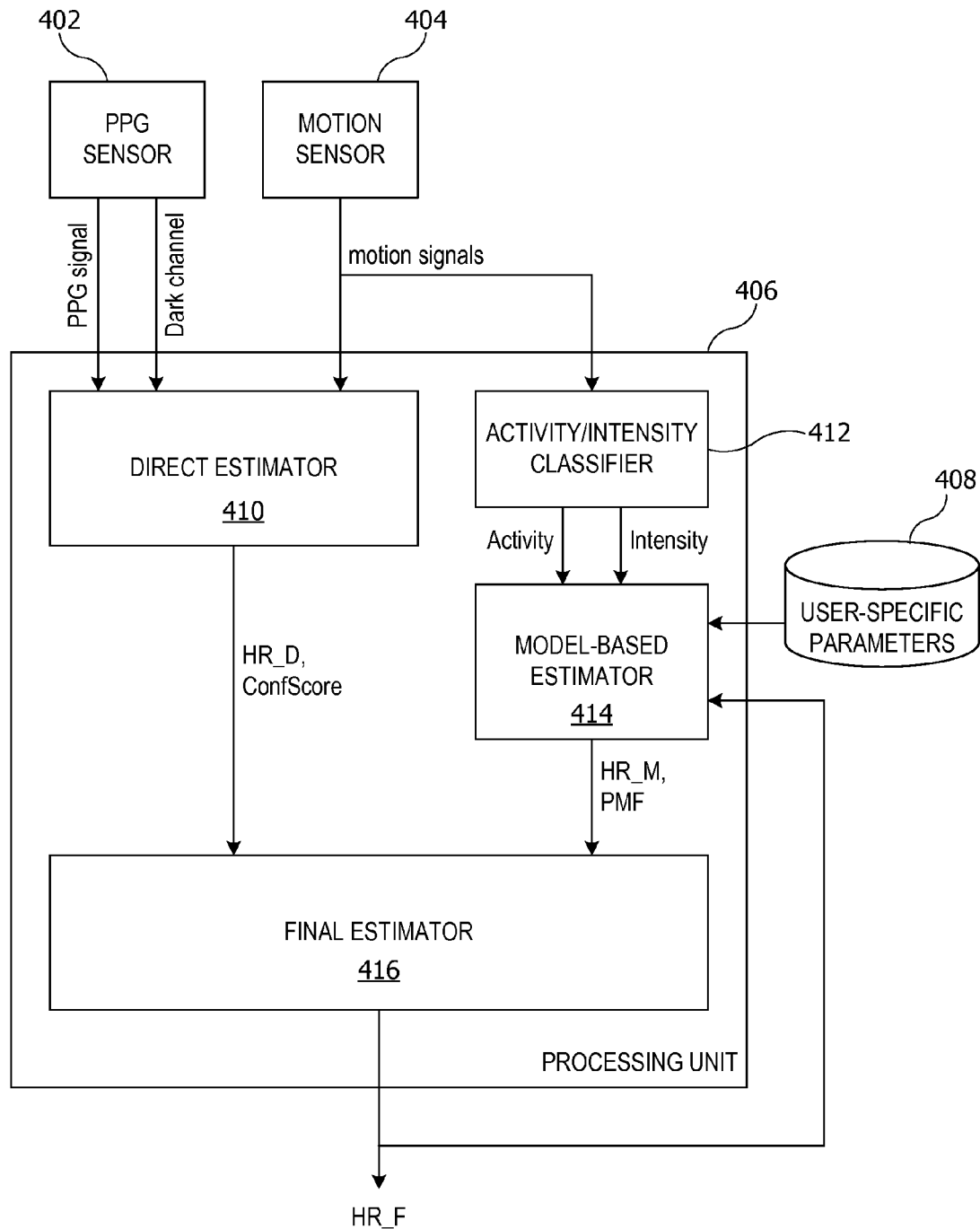
FIG. 4 is a simplified block diagram of a system for estimating heart rate according to an embodiment of the present invention.

FIG. 4 is a simplified block diagram of a system 400 for estimating heart rate according to an embodiment of the present invention. System 400 can be implemented, e.g., in wearable device 102 described above. System 400 can include PPG sensor 402, motion sensor 404, processing unit 406 and data store 408.

PPG sensor 402 can be similar or identical to PPG sensor 300 described above. Motion sensor 404 can include any sensor capable of detecting motion of wearable device 102 (or more generally any device in which system 400 is implemented). For example, motion sensor 404 can include an accelerometer, a gyroscopic sensor, or the like.

Processing unit 406 can be implemented using a microprocessor, microcontroller, digital signal processor, or the like, which can be of generally conventional design, and/or other logic circuitry. For purposes of estimating a user's heart rate, processing unit 406 can include a direct estimator module 410, an activity and intensity classifier module 412, a model-based estimator module 414, and a final estimator module 416.

Direct estimator module 410 can analyze inputs including signals from PPG sensor 402 and motion sensor 404 and can compute a "direct" heart rate estimate (HR_D) as well as a confidence score (ConfScore). For example, direct estimator module 410 can apply various noise-reduction techniques to a PPG signal received from PPG sensor 402. Such techniques can include using a dark channel signal received from PPG sensor 402 to reduce noise (e.g., as described below) and/or using motion signals received from motion sensor 404 to reduce motion artifacts. An example of a specific process that can be implemented in direct estimator module 410 is described below.

Activity and intensity classifier 412 can analyze inputs including signals from motion sensor 404 to determine the user's current activity and intensity of the activity. For example, activity and intensity classifier 412 can receive data from motion sensor 404 and optionally other sensors, including biometric sensors. In some embodiments, activity and intensity classifier 412 can receive data derived from various sensors, such as a heart rate estimate (e.g., from any or all of direct estimator 410, model-based estimator 414, and/or final estimator 410), a stride length estimate (which can be determined in any manner desired), or a calorie-consumption estimate (which can also be determined in any manner desired). Activity and intensity classifier 412 can analyze the received data to determine the type of activity in which the user is most likely engaged, e.g., walking, sitting or standing still, jogging, running, cycling, riding in a motor vehicle and so on. In some instances, activity and intensity classifier 412 can also determine a measure of the intensity associated with the activity, such as an average speed or stride rate (or cadence) if the user is engaged in a repetitive movement (e.g., walking, jogging, running, cycling, etc.). Activity and intensity classifier 412 can implement machine learning algorithms that identify characteristic motion-sensor features associated with various types of activity, and the algorithms can be trained by gathering sensor data during known user activities prior to deploying activity and intensity classifier 412. In some embodiments, activity and intensity classifier 412 can compute a probability of the user being engaged in each of a number of recognized activities and can output a probability vector rather than a single activity indicator. Specific examples of operations that can be implemented in activity and intensity classifier 412 are described in above-referenced U.S. Provisional Application No. 62/004,707.

Model-based estimator 414 can receive the activity and intensity determinations (also referred to herein as an "activity context") from activity and intensity classifier 412. Based on this information and a physiological model of how a user's heart rate is expected to respond to activity and changes in activity, model-based estimator 414 can compute a "model-based" (or "modeled") heart rate estimate (HR_M) and/or a probability distribution (such as a probability mass function, or PMF) representing the likelihood of a user having a particular heart rate at a given time, based on knowledge of the user's present and previous activity context. In some embodiments, the model can be informed by various user-specific parameters that can be stored in data store 408. Examples of user-specific parameters include the user's age, gender, weight, general level of physical fitness, and/or previous measurements of heart rate or heart rate evolution during various activities. While user-specific parameters are not required, to the extent they are available, the physiological model used to produced modeled heart rate estimate HR_M can be more accurately tailored to the particular user. Specific examples of physiological models and processing algorithms are described below.

Final estimator 416 can use both direct heart rate estimate HR_D and modeled heart rate estimate HR_M to determine a final heart rate estimate (HR_F). In some embodiments, the determination can be based in part on confidence score ConfScore associated with direct heart rate estimate HR_D and/or the probability distribution (e.g., PMF) associated with the modeled heart rate estimate HR_M. For example, higher (lower) confidence in direct heart rate estimate HR_D can result in less (more) reliance on modeled heart rate estimate HR_M.

Final heart rate estimate HR_F can be used in any manner desired. For example, final heart rate estimate HR_F can be presented to the user (e.g., as shown in FIG. 2A). Final heart rate estimate HR_F can also be logged along with other activity-specific data (e.g., duration of workout, distance traveled, step count or stride count, etc.) for later review and/or reporting. Final heart rate estimate HR_F can also be provided to other activity analysis modules or processes, such as a process for estimating the user's calorie (energy) consumption. In some embodiments, final heart rate estimate HR_F can be used as an input to activity and intensity classifier 412, for instance, when confidence score ConfScore is high.

Further, in some embodiments final heart rate estimate HR_F can also be used as a feedback input to model-based estimator 414. For instance, when final heart rate estimate HR_F is considered highly reliable (e.g., when confidence score ConfScore is high), final heart rate estimate HR_F can be stored as a previous heart rate measurement for the current activity in user-specific parameters data store 408.

It will be appreciated that system 400 is illustrative and that variations and modifications are possible. System 400 can be incorporated into wearable device 102 and/or any number of other devices having a variety of form factors. For instance, in some embodiments, processing unit 406 can be disposed within a housing of one device, and sensors such as PPG sensor 402 and/or motion sensor 404 can be disposed in a physically distinct device. Further, while system 400 is described with reference to particular blocks, it is to be understood that these blocks are defined for convenience of description and are not intended to imply a particular physical arrangement of component parts. Further, the blocks need not correspond to physically distinct components, and the same physical components can be used to implement aspects of multiple blocks. Blocks can be configured to perform various operations, e.g., by programming a processor or providing appropriate control circuitry, and various blocks might or might not be reconfigurable depending on how the initial configuration is obtained. Embodiments of the present invention can be realized in a variety of apparatus including electronic devices implemented using any combination of circuitry and software.

Examples of processing algorithms that can be implemented in system 400 will now be described. These algorithms can be executed at regular intervals (e.g., once per second, once every five seconds, or the like) to provide a periodically updated real-time heart rate estimate.

Figure 5:
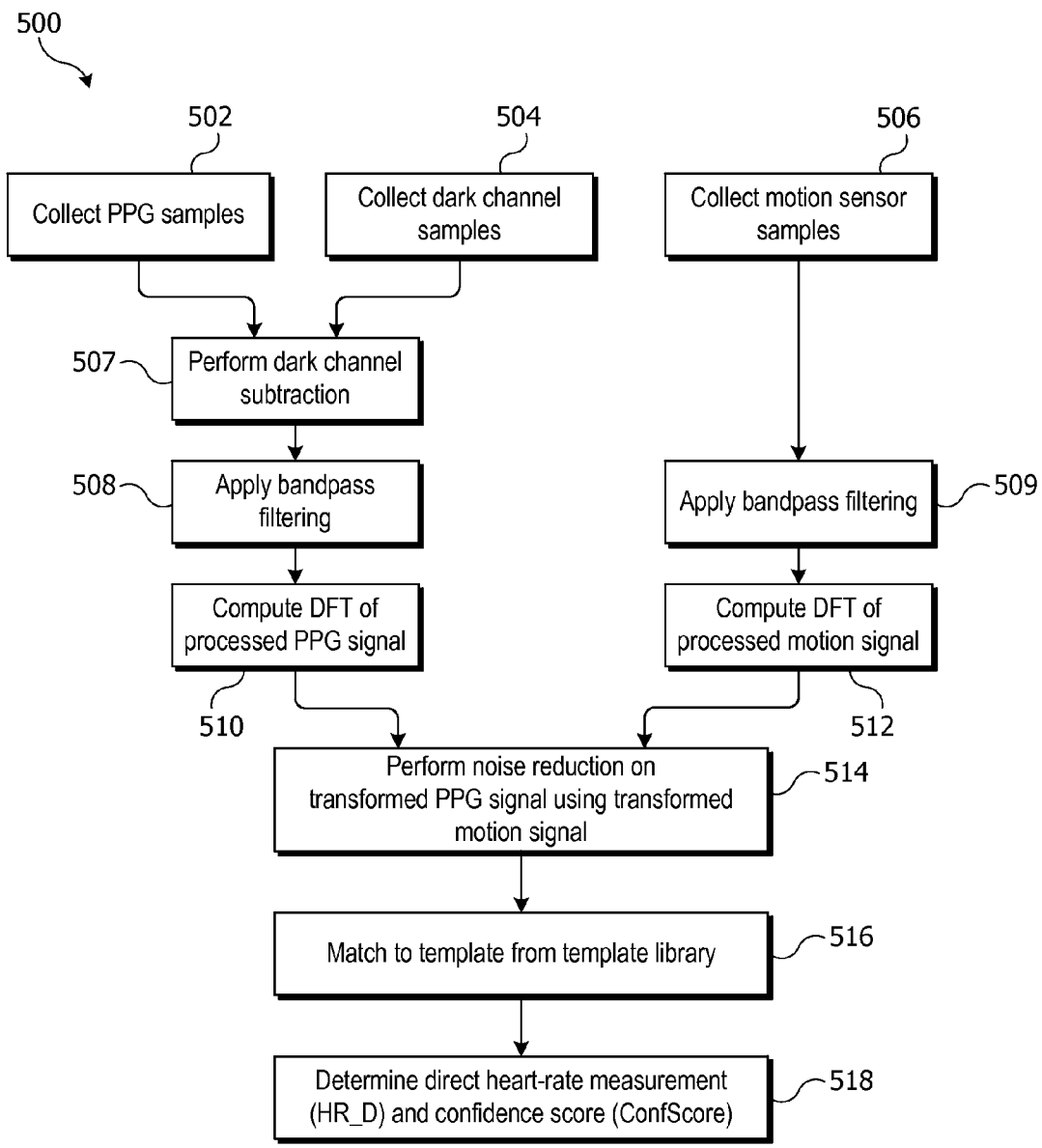
FIG. 5 is a flow diagram of a process for generating a direct heart rate estimate according to an embodiment of the present invention.

FIG. 5 is a flow diagram of a process 500 that can be implemented, e.g., in direct estimator module 410 of processing unit 406 according to an embodiment of the present invention. Process 500 uses PPG sensor signals and other signals to produce a "direct" estimate of the user's heart rate. The estimate is referred to as "direct" to indicate that it is based on sensor data and independent of a physiological model.

At blocks 502, 504, and 506, sensor data samples can be collected using various sensors to produce various sensor data streams. For instance, at block 502, a stream of PPG samples can be collected, e.g., using PPG sensor 402 of FIG. 4. At block 504, a stream of dark channel samples can be collected, e.g., also using PPG sensor 402 of FIG. 4. At block 506, a stream of motion sensor data samples can be collected, e.g., using motion sensor 404 of FIG. 4. Collection of data samples for the various streams can be concurrent, though not necessarily simultaneous.

In some embodiments, data samples can be collected in a synchronous or quasi-synchronous fashion so that data samples for the various data streams are either coincident in time or can be interpolated to produce streams of time-coincident samples. For example, PPG sensor 402 can be operated in a time-division multiplexed fashion such that, for each sampling interval, its light source is on for an first phase of the interval to collect one or more PPG samples (corresponding to block 502) and off for a second phase of the interval to collect one or more dark-channel samples (corresponding to block 504). The timing of sample collection can be controlled using a PPG sampling clock. For example, the sampling interval can be 1/256 second, during which 8 PPG samples and 8 dark-channel samples can be collected; other sampling intervals and sampling rates can be used. Motion sensor data samples can be collected by sampling the relevant sensors at times controlled using the PPG sampling clock, or by using a separate sampling clock and interpolating the sample stream to produce samples coincident in time with the PPG samples.

At block 507, dark-channel subtraction can be performed on the PPG and dark-channel sample data streams to subtract dark channel samples from the PPG samples. The dark-channel sample stream can be regarded as an estimate of background luminosity that is common to both the PPG samples and dark channel samples. Such background luminosity can be regarded as nuisance noise.

At blocks 508 and 509, the dark-channel-subtracted PPG signal and the motion-sensor signal can be separately bandpass filtered to reduce frequency content outside the range where most of the energy of a signal driven by a heart pumping would be expected to reside. For example, in one embodiment, a filter that attenuates frequency content below 0.5 Hz and above 6 Hz may be deployed.

At blocks 510 and 512, the processed signals can be transformed to frequency space, e.g., using a discrete Fourier transform (DFT). Effects of small temporal misalignments incurred during sample collection be reduced by using the frequency domain. Further, since the quantity of primary interest in process 500 is the user's heart rate (which is a frequency-specified quantity), a frequency-domain analysis can be more directly useful than a time-domain analysis.

At block 514, noise reduction can be performed on the transformed PPG signal using the transformed motion sensor signal artifacts. For example, assuming the user is engaged in an activity that involves repetitive movement (e.g., running, walking, swimming, rowing), the motion-sensor signal may have frequency resonances corresponding to the frequency of the movement (and multiples or submultiples thereof). Accordingly, judicious subtraction of the transformed motion sensor signal from the transformed PPG signal can reduce motion-related noise. Other noise-reduction techniques can also be used.

At block 516, the noise-reduced PPG signal can be further analyzed to identify dominant frequency peaks, one of which in theory should correspond to the user's heart rate. It is to be understood that the noise-reduced PPG signal may still have some noise contamination, and the most dominant frequency might not correlate to the user's heart rate. In some embodiments, rather than using the most dominant frequency, a template-matching technique can be used. For example, a steady pulse can be represented as a low-order Fourier series (e.g., fourth-order, with eight coefficients plus a frequency parameter). The cleaned-up PPG signal can be correlated to templates corresponding to Fourier series with different possible heart rates (e.g., with a granularity of 1 or 2 beats per minute); the strongest correlation will be expected to occur for the template closest to the actual heart rate. Additional examples of processes that can be used are described in above-referenced U.S. Provisional Application No. 62/040,967.

At block 518, the direct heart rate estimate (HR_D) and confidence score (ConfScore) can be determined. For example, HR_D can correspond to the template heart rate that provided the best match, and confidence score ConfScore can be based on the degree or strength of the correlation with the best matching template. Since any residual noise remaining after noise reduction at block 514 would tend to weaken the correlation with the "correct" template (i.e., the one that corresponds to the user's actual heart rate), ConfScore can reflect the amount of noise remaining in the signal and therefore the reliability of the signal.

It will be appreciated that process 500 is illustrative and that variations and modifications are possible. Steps described as sequential may be executed in parallel, order of steps may be varied, and steps may be modified, combined, added or omitted. Other noise reduction techniques can be applied, and other analysis techniques can be applied in addition to or instead of template matching to determine a direct heart rate estimate. Further, other types of pulse-monitoring sensors can be substituted for PPG sensors.

Process 500 determines a heart rate estimate based on a signal from a pulse sensor (e.g., a PPG sensor). In many circumstances, a reliable estimate can be obtained. However, the reliability might not be perfect, e.g., due to residual noise. Accordingly, further improvement can be had by using a model-based heart rate estimate to guide the final heart rate estimator. In some embodiments, model-based estimator module 414 of FIG. 4 can implement a model-based approach that predicts a heart rate based on information about the user's current and previous activities, applied to a model of the user's physiological response to activity.

Figure 6:
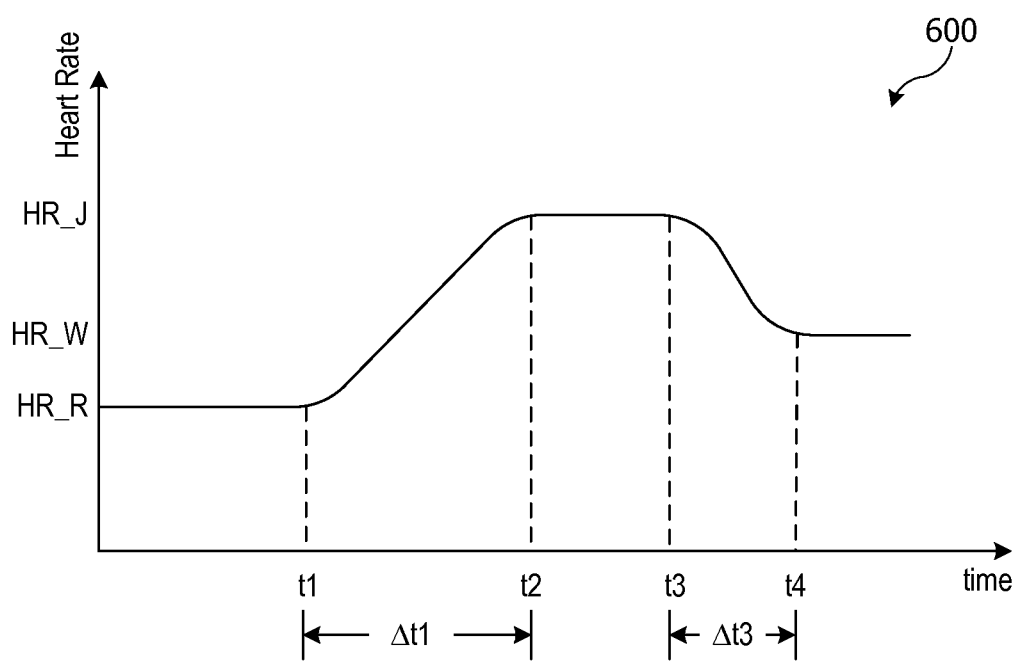
FIG. 6 is a graph illustrating a physiological model of heart rate response that can be used in an embodiment of the present invention.

FIG. 6 is a graph 600 illustrating a physiological model of heart rate response (vertical axis) to activity as a function of time (horizontal axis) that can be used in an embodiment of the present invention. It is known from numerous studies that, if a constant activity level is maintained over a period of time, an individual's heart rate tends toward a stable (equilibrium) value associated with that activity. The specific equilibrium value generally depends on the activity, environmental factors (e.g., ambient temperature), and on the particular user (e.g., the user's age and physical fitness level), but for any user, some equilibrium value is expected. If the activity changes, the heart rate tends to migrate monotonically (on average) toward the equilibrium value associated with the new activity. For example, in FIG. 6, at time 0, the user is at rest and has a resting heart rate (HR_R) that remains essentially constant (ignoring natural heart rate variability) as long as the user remains at rest. At time t1, the user begins to engage in an activity, e.g., jogging, and the user's heart rate ramps to an equilibrium value (HR_J) associated with jogging. At time t2, the heart rate reaches the equilibrium value and stabilizes there. At time t3, the user slows down to walking speed, and the heart rate ramps down to a lower equilibrium value (HR_W) associated with walking, stabilizing at that value at a time t4. The transition times ($\Delta t1 = t2 - t0$ and $\Delta t3 = t3 - t2$) and the particular equilibrium heart rates (HR_0, HR_J, HR_W) generally depend on the user's age and fitness level. In some embodiments, these parameters can be learned over time using feedback from final heart rate estimator module 416 as described below. It should be understood that the migration of heart rate to a new equilibrium value need not be linear in time. For example, it may be that the trajectory more closely follows a model based on exponential behavior.

Given suitable user-specific parameters and knowledge of the user's current and prior activity, the user's heart rate at a given time can be modeled using the physiological assumptions shown in FIG. 6. For example, in some embodiments, activity classifier 412 can generate an activity context (e.g., an estimate of the user's current activity and intensity) in real-time. Thus, activity classifier 412 may indicate that the user is walking at a speed of 3 miles per hour, running at a speed of 5 miles per hour, running at a speed of 7 miles per hour, resting, and so on. The activity context can be updated in real time at regular intervals (e.g., every 1 second, every 5 seconds, every 8 seconds).

User-specific parameters (e.g., in data store 408) can provide information about the user's equilibrium heart rate and transition times for various activities and intensities. In some embodiments, the user-specific parameters can be initialized based on general information about the user that can be obtained during device setup. Examples of general information include demographic characteristics such as age and gender, or a self-rating of the user's general physical fitness level. As the user wears the device during various activities and heart rate and other physiological information is gathered, the parameters can be updated based on the gathered information, allowing the physiological model to be tuned to the individual user. For instance, in some embodiments, the device can estimate the user's maximum oxygen consumption ($VO_2$ max) or other measurements of general physical fitness, and these measurements can be used to modify equilibrium heart rate and/or transition time parameters based on known physiological principles, such as that a user who is more physically fit will generally have a lower heart rate at a given activity level or a faster transition time between activities. Further, as the user's fitness level changes over time, tuning of the user-specific parameters can continue so that the estimates remain accurate.

Figure 7:
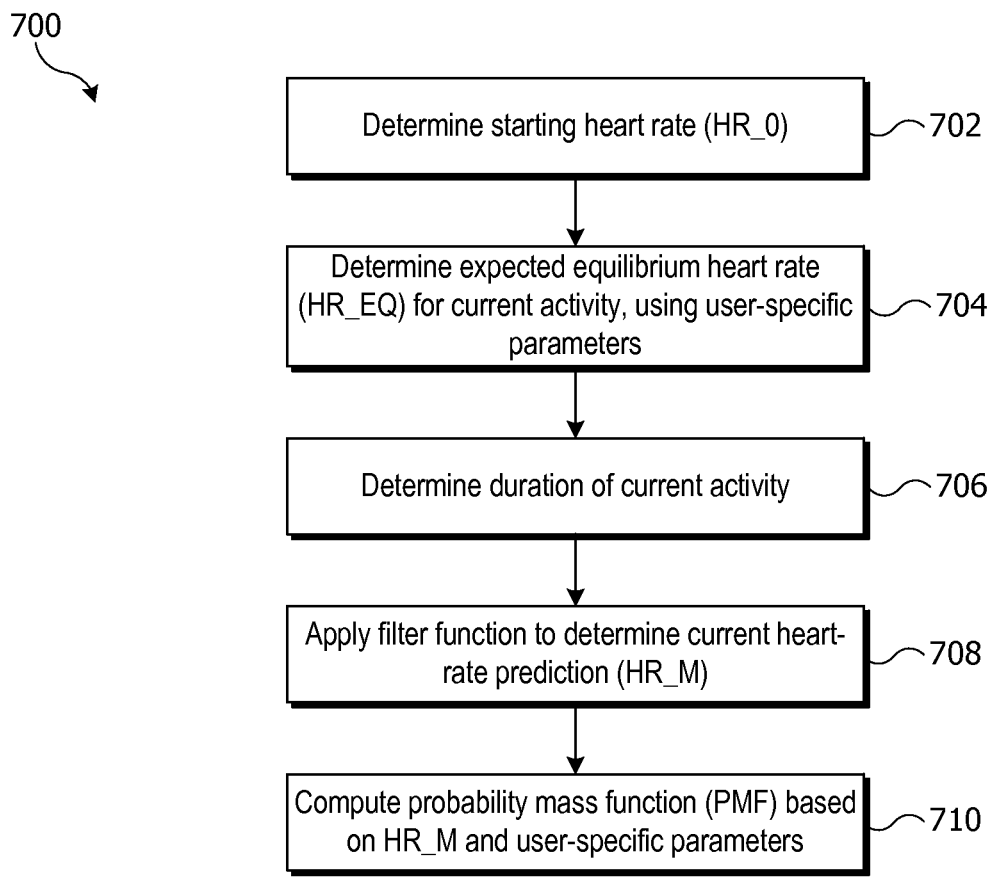
FIG. 7 is a flow diagram of a process for generating a model-based heart rate estimate according to an embodiment of the present invention.

FIG. 7 is a flow diagram of a process 700 for generating a model-based heart rate estimate according to an embodiment of the present invention. Process 700 can be implemented, e.g., in model-based estimator 414 of FIG. 4. Process 700 uses a physiological model of the kind shown in FIG. 6, together with an activity context (e.g., activity and intensity information from activity classifier 412 of FIG. 4) to produce a "modeled" estimate of the user's heart rate. The estimate is referred to as "modeled" (or model-based) to indicate that it is based on a physiological model and independent of pulse sensor readings.

At block 702, process 700 can determine a "starting" heart rate (HR_0), which can correspond to the user's heart rate at the time the user commenced a current activity. For example, model-based estimator 414 can receive activity and intensity signals from activity and intensity classifier 412 and can detect a change in activity based on a change in the received activity and intensity signals. A heart rate estimate (HR_F) that was produced by final estimator 416 just before the most recent activity change can be used as the starting heart rate HR_0. Alternatively, an equilibrium heart rate associated with the previous activity can be used.

At block 704, process 700 can determine an expected equilibrium heart rate (HR_EQ) for the current activity. The determination can be based on user-specific parameters, such as age, gender, fitness level, and/or previously measured heart rates associated with the user performing the current activity at or near the current intensity. Such parameters can be stored, e.g., in user-specific parameters data store 408, and accessed at block 704. In some embodiments where the activity context provided by activity and intensity classifier 412 includes a probability vector indicating the probability of each of multiple different activities (or intensities), the expected equilibrium heart rate can be determined using a probability-weighted average of equilibrium heart rates associated with two or more activities.

At block 706, process 700 can determine a duration of the current activity. For instance, model-based estimator 414 can keep track of the time elapsed since the last change in the received activity context.

At block 708, process 700 can apply a filter function to determine a current heart rate prediction (HR_M), also referred to as a model-based (or modeled) heart rate. The filter function can be based on a physiological model of the transition in heart rate with an activity change. As described above, it can be assumed that, for constant activity, the user's heart rate will reach and maintain an equilibrium value. The time needed for the heart rate to reach the equilibrium value after a change in activity as well as the actual equilibrium heart rate will generally depend on the user's level of physical fitness. Accordingly, the filter function can be user-dependent.

In some embodiments, the filter function can be a linear filter, with a slope (or transition time) based on the user's fitness level (or previously determined transition times for various activity changes). For example, heart rate response to a change in activity can be modeled using a difference equation such as:

$$HR\_M(t)=HR\_EQ((1-\alpha)+\alpha*HR\_M(t-1)), \quad (1)$$

where t is a sampling time and $\alpha$ is a transient characteristic based on the model-predicted transition time from HR_0 to HR_EQ. A filter function (e.g., a linear filter) can be derived from this model, using known techniques, and applied to determine a modeled heart rate at time t.

At block 710, process 700 can compute a probability mass function (PMF) based on HR_M and a range of heart rates within which HR_M is expected to lie. For example, a minimum expected heart rate (HRmin) and a maximum expected heart rate (HRmax) can be defined, such that the user's heart rate for the current activity is expected to always be somewhere in the range between HRmin and HRmax. In some embodiments, HRmin and HRmax can be based on general characteristics of the user, such as age and fitness level, as well as the current activity. They can also be based on previous measurements of the user's heart rate when performing the current activity.

The probability mass function can be generated, e.g., by applying a windowing function to the expected range and assuming a peak at the model-based heart rate HR_M. Various windowing functions can be used. One example is a Hanning window, defined by the equation:

$$w(n)=\tfrac{1}{2}[1-\cos 2\pi((n+1)/(N+1))], \quad (2)$$

where window width N can correspond to the range [HRmin, HRmax], and the step size n can correspond to the desired granularity of measurement, e.g., one beat per minute. In some embodiments, a lower half-window can be defined using a first Hanning window centered on HR_M and having a width equal to (HR_M−HRmin) and an upper half-window can be defined using a second Hanning window centered on HR_M and having a width equal to (HRmax−HR_M). Thus, the probability mass function can be asymmetric if desired.

It will be appreciated that process 700 is illustrative and that variations and modifications are possible. Steps described as sequential may be executed in parallel, order of steps may be varied, and steps may be modified, combined, added or omitted. Other filter functions and windowing functions can be substituted.

In some embodiments, model-based heart rate HR_M and probability mass function PMF produced by process 700 can be used to refine the direct heart rate estimate HR_D. For instance, as shown in FIG. 4, final estimator 416 can use the information provided by direct estimator 410 and model-based estimator 412 to compute a final heart rate estimate HR_F.

Figure 8:
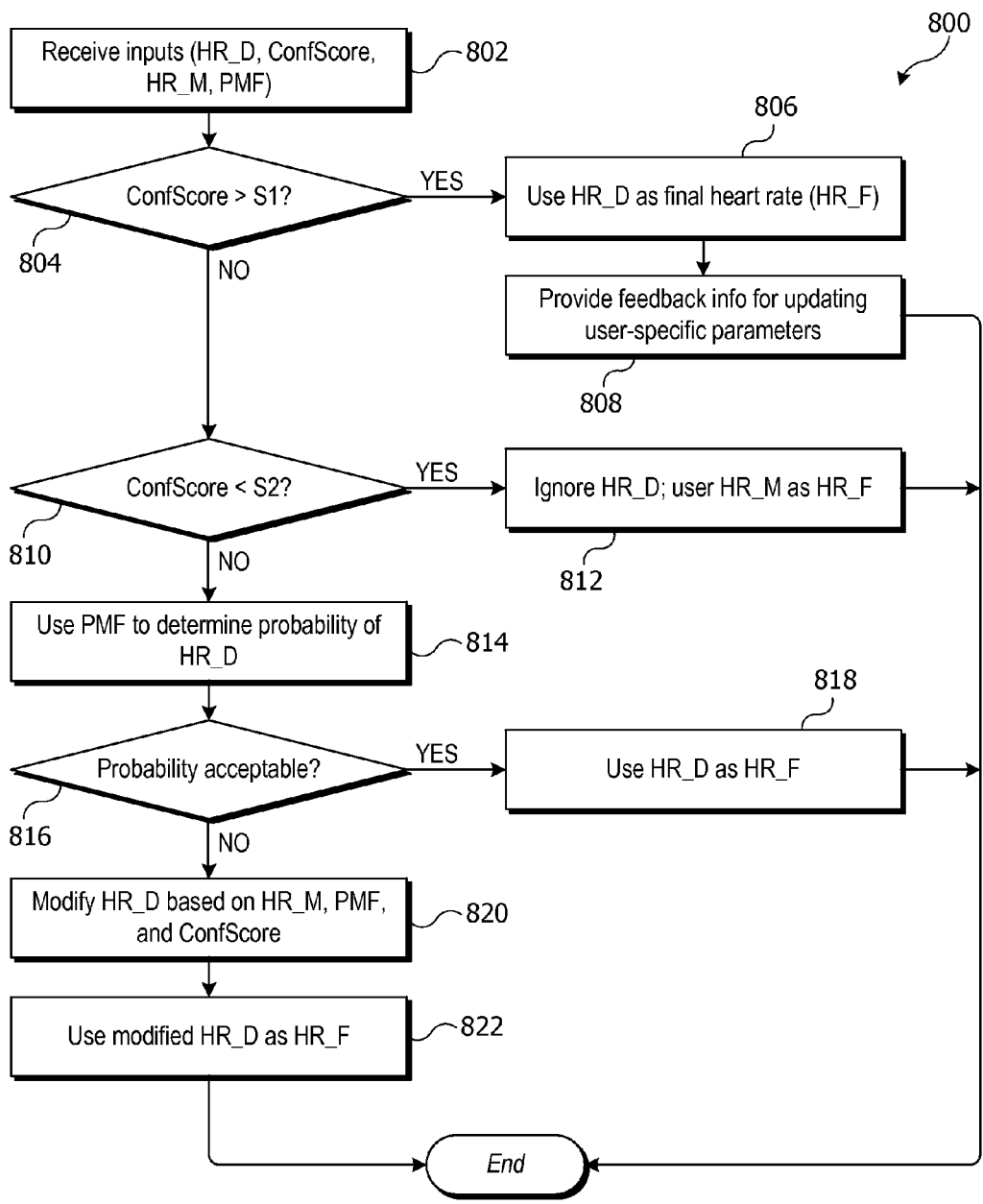
FIG. 8 is a flow diagram of a process for computing a final heart rate estimate according to an embodiment of the present invention.

FIG. 8 is a flow diagram of a process 800 for computing a final heart rate estimate according to an embodiment of the present invention. Process 800 can be implemented, e.g., in final estimator 416 of FIG. 4. In this example, process 800 can use model-based information to evaluate the reliability of a direct heart rate estimate. If the direct heart rate estimate is sufficiently reliable, then it is used as the final heart rate estimate. If not, the model-based information can be used to modify the direct heart rate estimate.

At block 802, process 800 can receive inputs including a direct heart rate estimate (HR_D) and associated confidence score (ConfScore) as well as a model-based heart rate estimate (HR_M) and associated probability mass function (PMF). For example, direct estimator module 410 can provide HR_D and ConfScore while model-based estimator module 414 provides HR_M and PMF.

At block 804, process 800 can determine whether direct heart rate estimate HR_D is highly reliable, for example, whether the confidence score ConfScore associated with HR_D exceeds a first threshold (S1). Threshold S1 can be set to a high confidence score (e.g., a 90% or 95% confidence level). If direct heart rate estimate HR_D is deemed highly reliable, then at block 806, HR_D can be used as the final heart rate estimate HR_F. At block 808, the final heart rate estimate HR_F can be used to provide feedback to model-based estimator module 414, e.g., for purposes of updating user-specific parameters stored in data store 408. Examples of updating user-specific parameters are described below.

If, at block 804, direct heart rate estimate HR_D is not deemed highly reliable, then at block 810, process 800 can determine whether direct heart rate estimate HR_D is deemed unreliable, for example, whether the confidence score ConfScore associated with HR_D is below a second threshold (S2). Threshold S2 can be set to a low confidence score (e.g., 10% or 20% confidence level). If direct heart rate estimate HR_D is deemed unreliable, then at block 812, HR_D can be ignored, and model-based heart rate estimate HR_M can be used as the final heart rate HR_F.

If, at block 810, direct heart rate estimate HR_D is not deemed unreliable, model-based information can be used to improve the reliability of the heart rate estimate. For example, at block 814, the model-based probability mass function (PMF) can be used to determine a probability of HR_D.

If, at block 816, the probability exceeds a threshold, for example 90% likelihood or greater, then at block 818, direct heart rate estimate HR_D can be used as final heart rate estimate HR_F. If not, then at block 820, direct heart rate estimate HR_D can be modified based on model-based heart rate estimate HR_M, probability mass function PMF, and confidence score ConfScore. For example, a weighted average can be computed based on the new value of HR_D and HR_M in conjunction with their associated probabilities, which can be determined from ConfScore and PMF, respectively. Denoting the probabilities associated with HR_D and HR_M as P_D and P_M, respectively, the weightings can be computed as:

$$W\_D=P\_D/(P\_D+P\_M) \quad (3)$$

and $$W\_M=PM/(P\_D+P\_M). \quad (4)$$

The modified heart rate estimate, HR_D', can be computed as:

$$HR\_D'=W\_D*HR\_D+W\_M*HR\_M. \quad (5)$$

At block 822, the modified heart rate estimate can be used as the final heart rate estimate HR_F.

It will be appreciated that process 800 is illustrative and that variations and modifications are possible. Steps described as sequential may be executed in parallel, order of steps may be varied, and steps may be modified, combined, added or omitted. For instance, in some embodiments, the model-based probability mass function can be used to reject HR_D if HR_D is outside a range allowed by the probability mass function, regardless of the confidence score assigned to HR_D. Other criteria can also be applied to reject or modify a direct heart rate estimate, such as an implausibly large jump in HR_D from one measurement cycle to the next, significant decrease (increase) in HR_D from one cycle to the next when the physiological model predicts increasing (decreasing) heart rate, or the like.

In some embodiments, direct estimator module 410 can provide as outputs a list of candidate heart rates HR_D and a confidence score for each, based on template matching or other techniques. If two or more possible heart rates have similar confidence scores, final estimator module 416 can use the probability mass function to select the most probable candidate HR_D as the final heart rate estimate HR_F.

As noted above, the final heart rate estimate can be used to update the user-specific parameters stored in data store 408. For instance, in cases where a highly reliable direct heart rate estimate HR_D is available, HR_D can be treated as indicating the user's actual heart rate during the current activity. If HR_D remains reasonably stable and reliable during a period of constant activity, it can provide a direct measurement of the equilibrium heart rate for the user performing that specific activity. In some embodiments, old and new measurements of the user's equilibrium heart rate for a particular activity can be averaged using a time-weighted average, such that more recent measurements are accorded greater weight. In some embodiments, confidence scores can also be incorporated into the weighting. In a similar manner, transition times between various activities can be determined based on the availability of reliable direct heart rate estimates HR_D during the transition. Such feedback can allow the accuracy of heart rate determination system 400 to improve over time as the system learns about the user. Further, such feedback can allow heart rate determination system 400 to evolve to reflect changes in the user's fitness level over time.

Figure 9:
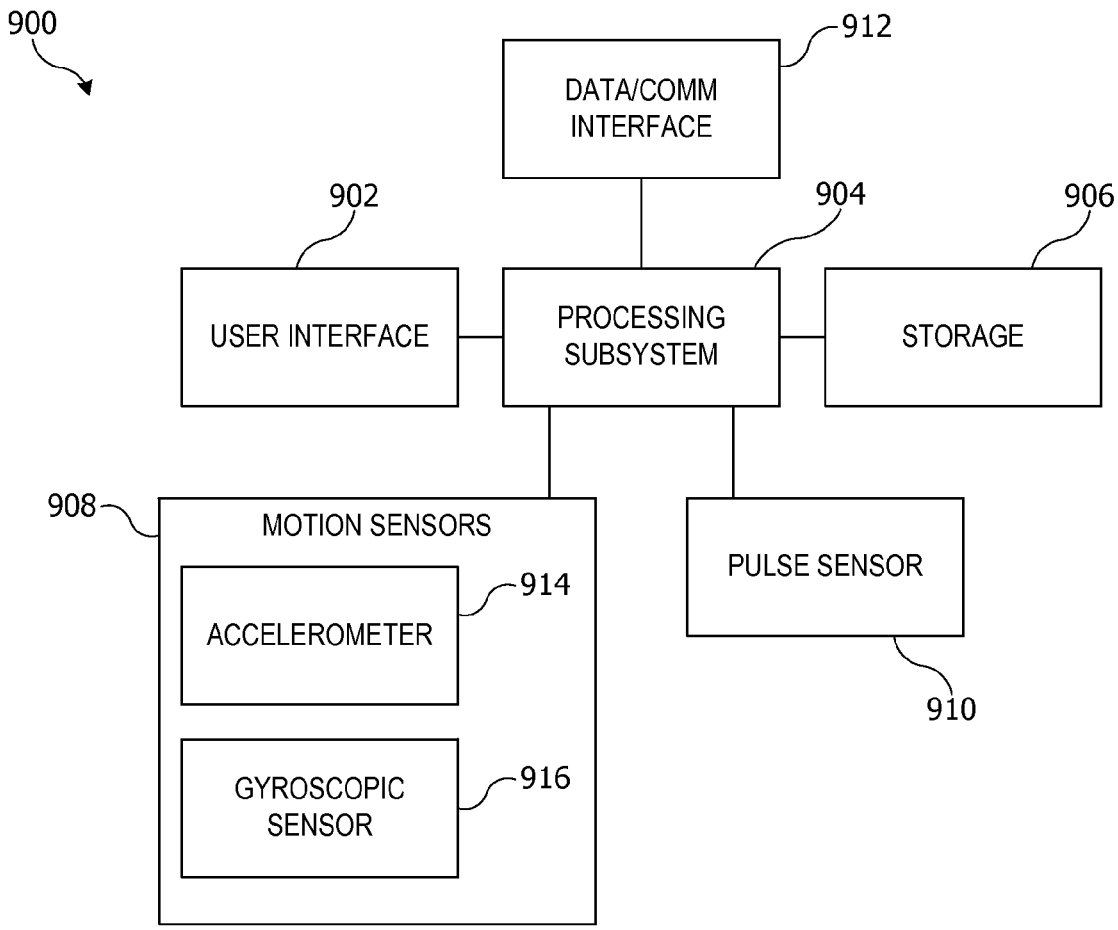
FIG. 9 is a block diagram showing components of a device according to an embodiment of the present invention.

Heart rate estimation techniques as described above can be implemented in a variety of electronic devices, including wearable devices having a pulse sensor and non-wearable devices that can communicate with a pulse sensor (which can be wearable). FIG. 9 is a block diagram showing components of a device 900 according to an embodiment of the present invention. Device 900 can be, e.g., an implementation of device 102 and can incorporate system 400 described above. Device 900 can include a user interface 902, a processing subsystem 904, a storage subsystem 906, motion sensors 908, a pulse sensor 910, and a data and communication interface 912.

User interface 902 can incorporate hardware and software components that facilitate user interaction with device 900. Such components can be of generally conventional or other designs. For example, in some embodiments, user interface 902 can include a touch-screen interface that incorporates a display (e.g., LED-based, LCD-based, OLED-based, or the like) with a touch-sensitive overlay (e.g., capacitive or resistive) that can detect contact by a user's finger and/or other objects. By touching particular areas of the screen, the user can indicate actions to be taken, respond to visual prompts from the device, etc. In addition or instead, user interface 902 can include audio components (e.g., speakers, microphone); buttons; knobs; dials; haptic input or output devices; and so on.

Processing subsystem 904, which can be implemented using one or more integrated circuits of generally conventional or other designs (e.g., a programmable microcontroller or microprocessor with one or more cores), can be the primary processing subsystem of device 900. Storage subsystem 906 can be implemented using memory circuits (e.g., DRAM, SRAM, ROM, flash memory, or the like) or other computer-readable storage media and can store program instructions for execution by processing subsystem 904 as well as data generated by or supplied to device 900 in the course of its operations, such as user-specific parameters. For instance, storage subsystem 906 can implement data store 408 of FIG. 4. In operation, processing subsystem 904 can execute program instructions stored by storage subsystem 906 to control operation of device 900. For example, processing subsystem 904 can execute an operating system as well as various application programs specific to particular tasks (e.g., displaying the time, presenting information to the user, obtaining information from the user, communicating with a paired device, etc.). In some embodiments, processing subsystem 904 can implement the various estimator modules of processing unit 406 described above, as well as activity and intensity classifier 412. It is to be understood that processing subsystem 904 can execute any processing tasks desired.

Motion sensors 908 can include various sensors capable of detecting and/or characterizing movement of device 900. Examples include accelerometer 914 and gyroscopic sensor (also referred to as gyroscope) 916. Accelerometer 914 can be implemented using conventional or other designs and can be sensitive to accelerations experienced by device 900 (including gravitational acceleration as well as acceleration due to user motion) along one or more axes. In some embodiments, accelerometer 914 can incorporate a 3-axis low-power MEMS accelerometer and can provide acceleration data at a fixed sampling rate (e.g., 100 Hz). Gyroscope 916 can also be implemented using conventional or other designs and can be sensitive to changes in the orientation of device 900 along one or more axes. Gyroscope 916 can also provide orientation data at a fixed sampling rate (e.g., 100 Hz).

Pulse sensor 910 can include a PPG sensor (e.g., similar or identical to PPG sensor 300 described above), or another type of pulse sensor, such as an electrical pulse sensor. In some embodiments, pulse sensor 910 can include a component external to a housing of device 900 (e.g., a chest strap, wrist strap, or the like). The external component can generate signals based on a physical measurement (e.g., a PPG signal or a signal representing changes in electrical properties of the user's skin) and can transmit the signals to the rest of device 900 via wired or wireless channels as desired. Pulse sensor 910 can provide data at a fixed sampling rate (e.g., 10 Hz or the like).

Data and communication interface 912 can allow device 900 to communicate with other devices via wired and/or wireless communication channels. For example, data and communication interface 912 can include an RF transceiver and associated protocol stack implementing one or more wireless communication standards (e.g., Bluetooth standards; IEEE 802.11 family standards; cellular data network standards such as 3G, LTE; cellular voice standards, etc.). In addition or instead, data and communication interface 912 can include a wired communication interface such as a receptacle connector (e.g., supporting USB, UART, Ethernet, or other wired communication protocols). In some embodiments, data and communication interface 912 can allow device 900 to be paired with another personal electronic device of the user (also referred to as a "companion" device), such as a mobile phone, laptop or desktop computer, tablet computer, or the like. Via data and communication interface 912, device 900 can provide a record of heart rate estimates and associated activities (as well as any other information pertaining to the activity) to the companion device. This can allow the user to conveniently review workout data or other fitness-related information using a device with a larger screen. Further, in some embodiments, device 900 may retain a record of a series of heart rate estimates associated with various user activities until such time as the record is transferred to the companion device, after which device 900 can delete the record. This can reduce the amount of local storage required on device 900.

It will be appreciated that device 900 is illustrative and that variations and modifications are possible. Embodiments of device 900 can include other components in addition to or instead of those shown. For example, device 900 can include a power source (e.g., a battery) and power distribution and/or power management components. Device 900 can include other sensors, such as a compass, a thermometer or other external temperature sensor, a Global Positioning System (GPS) receiver or the like to determine absolute location, camera to capture images, biometric sensors (e.g., blood pressure sensor, skin conductance sensor, skin temperature sensor), and so on.

Further, while device 900 described with reference to particular blocks, it is to be understood that these blocks are defined for convenience of description and are not intended to imply a particular physical arrangement of component parts. Further, the blocks need not correspond to physically distinct components, and the same physical components can be used to implement aspects of multiple blocks. Blocks can be configured to perform various operations, e.g., by programming a processor or providing appropriate control circuitry, and various blocks might or might not be reconfigurable depending on how the initial configuration is obtained. Embodiments of the present invention can be realized in a variety of apparatus including electronic devices implemented using any combination of circuitry and software.

While the invention has been described with respect to specific embodiments, one skilled in the art will recognize that numerous modifications are possible. For instance while embodiments described above may make reference to a wrist-worn device, those skilled in the art will recognize that a pulse-sensing device can also be worn on a different area of the user's body and that techniques described herein can be used to estimate heart rate. Further, although specific embodiments described above use a PPG sensor to measure a pulse rate, other types of pulse sensors can be substituted. To the extent that such sensors are susceptible to noise that can interfere with accurately estimating heart rate, use of a physiologically-based model to guide the estimate (e.g., in the manner described above) can improve the accuracy of the estimate.

Embodiments of the present invention can be realized using any combination of dedicated components and/or programmable processors and/or other programmable devices. The various processes described herein can be implemented on the same processor or different processors in any combination. Where components are described as being configured to perform certain operations, such configuration can be accomplished, e.g., by designing electronic circuits to perform the operation, by programming programmable electronic circuits (such as microprocessors) to perform the operation, or any combination thereof. Further, while the embodiments described above may make reference to specific hardware and software components, those skilled in the art will appreciate that different combinations of hardware and/or software components may also be used and that particular operations described as being implemented in hardware might also be implemented in software or vice versa.

Computer programs incorporating various features of the present invention may be encoded and stored on various computer readable storage media; suitable media include magnetic disk or tape, optical storage media such as compact disk (CD) or DVD (digital versatile disk), flash memory, and other non-transitory media. (It is understood that "storage" of data is distinct from propagation of data using transitory media such as carrier waves.) Computer readable media encoded with the program code may be packaged with a compatible electronic device, or the program code may be provided separately from electronic devices (e.g., via Internet download or as a separately packaged computer readable storage medium).

Thus, although the invention has been described with respect to specific embodiments, it will be appreciated that the invention is intended to cover all modifications and equivalents within the scope of the following claims.

What is claimed is:

1. A method of determining a heart rate of a user, the method comprising, by a wearable device:
generating, using a pulse sensor of the wearable device, a sequence of heart rate data samples;
determining, using the sequence of heart rate data samples, a direct heart rate estimate;
determining an activity context of the wearable device, the activity context including a physical activity in which the user is engaged and an intensity of the physical activity;
generating, based in part on the activity context and in part on a user-specific parameter, a modeled heart rate estimate, the modeled heart rate estimate being based on a physiological model of heart rate response to the activity context and generated independently of the sequence of heart rate data samples; and
determining a final heart rate estimate based on the direct heart rate estimate and the modeled heart rate estimate.

2. The method of claim 1 wherein determining the direct heart rate estimate includes:
determining, using a motion sensor of the wearable device, a motion-related noise component; and
subtracting the motion-related noise component from the heart rate data samples.

3. The method of claim 1 wherein the pulse sensor includes a photoplethysmographic sensor and wherein determining the direct heart rate estimate includes:
measuring a dark channel signal for the photoplethysmographic sensor; and
subtracting the dark channel signal from the heart rate data samples.

4. The method of claim 1 wherein determining the direct heart rate estimate includes:
generating a frequency spectrum from the heart rate data samples;
comparing the generated frequency spectrum to each of a plurality of template spectra, each template spectrum corresponding to a different candidate heart rate; and
identifying a best matching template spectrum based on the comparing,
wherein the direct heart rate estimate is based on the best-matching template spectrum.

5. The method of claim 4 further comprising:
generating a confidence score for the direct heart rate estimate, the confidence score based at least in part on how well the generated frequency spectrum matches the best-matching template spectrum,
wherein determining the final heart rate estimate is based in part on the confidence score.

6. The method of claim 1 wherein the activity context includes an activity identifier and wherein generating the modeled heart rate estimate includes:
determining a starting time based on a most recent change in the activity identifier;
establishing a starting heart rate based on a heart rate determined prior to the starting time;
determining an equilibrium heart rate based at least in part on a current activity indicated by the activity identifier; and
applying a filter function to the starting heart rate and the equilibrium heart rate based on a current time and the starting time.

7. The method of claim 6 wherein the equilibrium heart rate is determined based in part on the current activity and in part on a user-specific parameter.

8. The method of claim 7 wherein the user-specific parameter includes a parameter indicating a demographic characteristic of the user.

9. The method of claim 7 wherein the user-specific parameter includes a parameter indicating a fitness level of the user.

10. The method of claim 7 wherein the user-specific parameter includes a previously determined user-specific equilibrium heart rate associated with the current activity.

11. The method of claim 1 wherein generating the modeled heart rate estimate includes generating a probability mass function indicating a probability of each of a plurality of possible heart rates,
wherein determining the final heart rate estimate is based in part on the probability mass function.

12. A device comprising:
a pulse sensor;
a motion sensor; and
a processor coupled to the pulse sensor and the motion sensor, the processor configured to:
obtain a sequence of heart rate data samples from the pulse sensor;
determine, based on the sequence of heart rate data samples, a direct heart rate estimate;
determine, based at least in part on data from the motion sensor, an activity context of the device, the activity context including a physical activity in which a user is engaged and an intensity of the physical activity;
generate, based in part on the activity context of the device and in part on a user-specific parameter, a modeled heart rate estimate, the modeled heart rate estimate being based on a physiological model of heart rate response to the activity context and generated independently of the sequence of heart rate data samples; and
determine a final heart rate estimate based on the direct heart rate estimate and the modeled heart rate estimate.

13. The device of claim 12 wherein the pulse sensor includes a photoplethysmographic (PPG) sensor.

14. The device of claim 12 wherein the motion sensor includes one or more of an accelerometer or a gyroscope.

15. The device of claim 12 further comprising a user interface coupled to the processor and operable to present the final heart rate estimate to the user.

16. The device of claim 12 wherein the physiological model includes a filter function to model a heart rate transition from a staring heart rate to an equilibrium heart rate associated with a current activity context of the device.

17. A computer-readable storage medium having stored thereon program instructions that, when executed by a processor, cause the processor to perform a method comprising:
obtaining a sequence of heart rate data samples for a user;
determining, using the sequence of heart rate data samples, a direct heart rate estimate;
determining an activity context for the user, the activity context including a physical activity in which the user is engaged and an intensity of the physical activity;
generating, based in part on the activity context and in part on a user-specific parameter, a modeled heart rate estimate, the modeled heart rate estimate being based on a physiological model of heart rate response to the activity context and generated independently of the sequence of heart rate data samples; and
determining a final heart rate estimate based at least in part on the direct heart rate estimate and the modeled heart rate estimate.

18. The computer-readable storage medium of claim 17 wherein the method further comprises:
updating the user-specific parameter based on the final heart rate estimate.

19. The computer-readable storage medium of claim 17 wherein the method further comprises:
determining a confidence score for the direct heart rate estimate; and
determining a probability mass function for the modeled heart rate estimate,
wherein the final heart rate estimate is based in part on the confidence score and the probability mass function.

* * * * *